United States Patent [19]

Phillion et al.

[11] Patent Number: 5,627,174
[45] Date of Patent: May 6, 1997

[54] FLUOROALKENYL COMPOUNDS AND THEIR USE AS PEST CONTROL AGENTS

[75] Inventors: Dennis P. Phillion, St. Charles; Peter G. Ruminski, Ballwin; Gopichand Yalamanchili, St. Louis, all of Mo.

[73] Assignee: Monsanto Company, St. Louis, Mo.

[21] Appl. No.: 447,871

[22] Filed: May 23, 1995

Related U.S. Application Data

[62] Division of Ser. No. 329,593, Oct. 26, 1994.

[51] Int. Cl.$^6$ .............................. A61K 31/66; C07F 9/09
[52] U.S. Cl. .............................. 514/134; 514/75; 514/76; 514/140; 514/143; 558/70; 562/8; 564/14; 568/14; 568/17
[58] Field of Search .............................. 514/75, 76, 118, 514/143, 134, 140; 558/70, 155, 156; 562/8; 570/123, 140, 141, 142; 568/14, 17; 564/14

[56] References Cited

U.S. PATENT DOCUMENTS

| | | | |
|---|---|---|---|
| 3,510,503 | 5/1970 | Brokke et al. | 260/455 |
| 3,654,333 | 4/1972 | Brokke et al. | 564/74 |
| 3,689,662 | 9/1972 | Brokke et al. | 558/230 |
| 3,780,050 | 12/1973 | Brokke | 548/221 |
| 4,404,398 | 9/1983 | DeLue | 562/598 |
| 4,876,285 | 10/1989 | Peake | 514/746 |
| 4,950,666 | 8/1990 | Peake et al. | 514/227.5 |
| 4,952,580 | 8/1990 | Martinez et al. | 514/236.2 |

FOREIGN PATENT DOCUMENTS

| | | |
|---|---|---|
| 0432861 | 6/1991 | European Pat. Off. . |
| 49-17858 | 12/1970 | Japan . |
| 56-62825 | 5/1981 | Japan . |
| 63-172440 | 7/1988 | Japan . |
| WO86/07590 | 12/1986 | WIPO . |
| WO92/15555 | 10/1992 | WIPO . |

OTHER PUBLICATIONS

Debao Su et al. *J. Am. Chem. Soc.*, 112, pp. 3152–3155, 1990.

Kawada et al., Development of a new Fungicide, Mepronil, *Journal of Pesticide Science*, vol. 10, 1985, 315–324.

Dalconale et al., "Selective Oxidation of Aldehydes to Carboxylic Acids with Sodium Chlorite–Hydrogen Peroxide," *J. Org. Chem.*, vol. 51, pp. 567–569 (1986).

Hu et al., "Reactions of Perhalocarbons. Part IX: Conversion of Per(Poly)Fluoroalkyl Halides into the Corresponding Carboxylic Acids with a Redox System," *J. Fluorine Chem.*, vol. 49, pp. 275–280 (1990).

Huang et al., "Studies on Sulfinatodehalogenation. XV. Sodium Dithionite–Initiated Addition of Per–and Polyfluoroalkyl Halides to Ethyl Vinyl Ether and Chemical Conversation of Products," *Chin. J. Chem.*, vol. 3, pp. 281–288 (1990). *Abstract* Only Abstract.

Nwauka et al., "The Oxidation of Aldehydes to Acids with Calcium Hypochlorite [Ca(OCl)$_2$]," *Tetrahedron Letters*, vol. 23, No. 31, pp. 3131–3134 (1982).

Yamada et al., "Oxidation of Aldehydes into Carboxylic Acids with Molecular Oxygen Using Nickel (II) Complex Catalyst," *Chemistry Letters*, pp. 5–8 (1991).

*Primary Examiner*—Yogendra N. Gupta
*Attorney, Agent, or Firm*—Joan V. Thierstein; Arnold, White & Durkee

[57] ABSTRACT

Fluorinated alkene compounds useful for and methods of controlling nematodes, insects, and acarids that prey on agricultural crops, these compounds having the general structure:

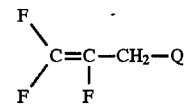

These Polar compounds are particularly useful for systemic control of pests.

9 Claims, No Drawings

FLUOROALKENYL COMPOUNDS AND THEIR USE AS PEST CONTROL AGENTS

This application is a divisional of U.S. Ser. No. 08/329,593 filed Oct. 26, 1994, now pending.

FIELD OF THE INVENTION

The present invention relates to certain fluoroalkenyl compounds, their derivatives and salts, and formulated compositions thereof. It also relates to methods of controlling pests that prey on agricultural crops, such as nematodes, insects, and acarids. New and efficient methods to prepare 3,4,4-trifluoro-3-butenoic acid, a key intermediate, are also provided.

BACKGROUND OF THE INVENTION

Fluorinated alkenes have long been known to control nematodes and insects when applied to the soil. U.S. Pat. Nos. 3,510,503, 3,654,333, and 3,780,050 all disclose such compounds. More recently, U.S. Pat. No. 4,952,580 disclosed polyhaloalkenes useful as nematocides, some of which were said to have some downward systemic activity, that is, would control to some extent nematode infestation of the root system afar application to the plant foliage. The majority of the compounds disclosed by these patents are nonpolar, which is a desirable characteristic for soil-applied pesticides, providing longer effective periods, but is much less effective for foliar application to achieve systemic effects. U.S. Pat. No. 4,950,666 discloses some polar difluoro-alkenylalkane compounds useful as systemic insecticides and nematocides. PCT Publication Number WO 92/15555 discloses fluoroakenyl compounds, including mono-, di- and trifluoroalkenylamines and trifluoroalkenyl-carboxylic acids for controlling pests such as nematodes, insects and acarids. However, there remains a need in the art for nematode, insect, and acarid control agents having improved systemic mobility, and desirably with low effective levels of use.

SUMMARY OF THE INVENTION

The present invention provides compounds, useful for controlling nematode, insect, and acrid infestation of a plant, having the structure (I):

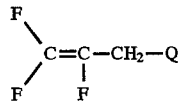

wherein
Q is -(C=S)-$R_1$, -(C=W)-$R_2$ or -(P=W)$R_3R_4$; wherein
W is O or S;
$R_1$ is -$OR_5$, -$SR_5$, halogen, -NHOH, or -$NR_5R_6$; wherein each of
$R_5$ and $R_6$ is independently
(i) hydrogen;
(ii) an aliphatic or an aromatic group, optionally substituted with at least one group selected from hydroxy, alkoxy, halo, nitro, amino, thiol, alkylthio, carboxyl, alkoxycarbonyl, and phenyl;
(iii) a $C_1$-$C_{12}$ aliphatic amine group, optionally substituted with at least one group selected from hydroxy, alkoxy, halo, nitro, amino, thiol, alkylthio, carboxyl, alkoxycarbonyl, and phenyl;
(iv) a $C_2$-$C_{12}$ aliphatic carboxylic add group, optionally substituted with at least one group selected from hydroxy, alkoxy, halo, nitro, amino, thiol, alkylthio, carboxyl, alkoxycarbonyl, and phenyl; or
(v) $R_5$ and $R_6$ taken together with the N of $R_1$ are a protein amino acid or a cyclic group selected from a radical of morpholine, piperidine, piperazine, or pyrrolidine, optionally substituted with at least one group selected from hydroxy, alkoxy, halo, nitro, amino, thiol, alkylthio, carboxyl, alkoxycarbonyl, and phenyl;

$R_2$ is
(a) an aliphatic or group, provided that W=O, each of which is optionally substituted with at least one group selected from a radical of sulfonic add, phosphonic acid, phosphinic acid, carboxylic acid, their esters, amides and thiol esters, cyano, trimethylsilyl, hydroxy, alkyl, alkoxy, halo, nitro, amino, thiol, alkylthio, and phenyl;
(b) -$OR_5$, -$SR_5$, or -$NR_5R_6$; wherein each of $R_5$ and $R_6$ is independently
(i) hydrogen,
(ii) an aliphatic, an aromatic, or a heterocyclic group, substituted with at least one group selected from a radical of sulfonic add, phosphonic acid, phosphinic acid, their esters, amides and thiol esters, cyano, trimethylsilyl and optionally further substituted with one of hydroxy, alkoxy, halo, nitro, amino, thiol, alkylthio, carboxyl, alkoxycarbonyl, or phenyl;
(iii) a $C_1$-$C_{12}$ aliphatic amine group substituted with at least one group selected from a radical of sulfonic acid, phosphonic add, phosphinic add, their esters, amides and thio esters, cyano, trimethylsilyl and optionally further substituted with one of hydroxy, alkoxy, halo, nitro, amino, thiol, alkylthio, carboxyl, alkoxycarbonyl, or phenyl;
(iv) a $C_2$-$C_{12}$ aliphatic carboxylic acid group, esters, amides and thio esters thereof, substituted with at least one group selected from a radical of sulfonic acid, phosphonic acid, phosphinic acid, their esters, amides and thiol esters, cyano, trimethylsilyl and optionally further substituted with one of hydroxy, alkoxy, halo, nitro, amino, thiol, alkylthio, carboxyl, alkoxycarbonyl, or phenyl;
(v) $R_5$ and $R_6$ taken together with the N of $R_2$ are a protein ,amino acid or a cyclic group selected from a radical of morpholine, piperidine, piperazine, or pyrrolidine, substituted with at least one group selected from a radical of sulfonic acid, phosphonic acid, phosphinic acid, their esters, amides and thio esters, cyano, trimethylailyl and optionally further substituted with one of hydroxy, alkoxy, halo, vitro, amino, thiol, alkylthio, carboxyl, alkoxycarbonyl, or phenyl;
(vi) $R_5$ and $_6$ taken together with the N of $R_2$ are pyrazole, imidazole or triazole, optionally substituted with at least one group selected from a radical of sulfonic acid, phosphonic acid, phosphinic acid, carboxylic acid, their esters, amides and thio esters, cyano, trimethylsilyl, hydroxy, alkoxy, halo, nitro, amino, thiol, alkylthio, or phenyl;
(vii) a heterocyclic group optionally substituted with at least one group selected from a radical of sulfonic acid, phosphonic acid, phosphinic acid, carboxylic acid, their esters, amides and thio esters, cyano, trimethylsilyl, hydroxy, alkoxy, halo, nitro, amino, thiol, alkylthio, or phenyl;
(viii) phenyl substituted by alkyl and optionally further substituted by a radical of sulfonic acid, phosphonic acid, phosphinic acid, carboxylic acid, their esters, amides and thio esters, cyano, trimethylsilyl, hydroxy, alkoxy, halo, vitro, amino, thiol, alkylthio, or phenyl;

(c) $NR_7R_8$; wherein $R_7$ is hydrogen, aliphatic or an aromatic group each of which is optionally substituted with at least one of the group of hydroxy, alkoxy, halo, vitro, amino, thiol, alkylthio, carboxyl esters, carboxyl amides, carboxyl thioesters or phenyl; $R_8$ is independently phenyl or substituted phenyl, —$OR_9$, —$C(O)R_9$, -$NR_9R_{10}$, -$S(O)_2R_{11}$, -$P(=O)R_{12}R_{13}$ where $R_9$ and $R_{10}$ are independently H, alkyl or aryl, $R_{11}$ is hydrogen, alkyl, haloalkyl or aryl, $R_{12}$ and $R_{13}$ are independently H, alkyl, aryl, alkoxy, aryloxy, alkylthio, arylthio, alkylamino, dialkylamino, arylamino, —$OR_{14}$ wherein $R_{14}$ is H, alkyl or aryl;

(d) a heterocyclic group optionally substituted with a radical of sulfonic acid, phosphonic acid, phosphinic acid, carboxylic acid, their esters, amides and thioesters, cyano, trimethylsilyl, hydroxy, alkoxy, halo, nitro, amino, thiol, alkylthio, or phenyl; with the proviso that when W=S, then the point of attachment to the heterocyclic group must be through a N atom;

(e) phenyl substituted by alkyl and optionally further substituted by a radical of sulfonic acid, phosphonic acid, phosphonic acid, carboxylic acid, their esters, amides and thioesters, cyano, trimethylsilyl, hydroxy, alkoxy, halo, nitro, amino, thiol, alkylthio, or phenyl, provided that W=O;

$R_3$ and $R_4$ are independently $R_{15}$, —$OR_{15}$, -$SR_{15}$, -$NR_{15}R_{16}$ where $R_{15}$ and $R_{16}$ are independently selected from the group consisting of hydrogen; an aliphatic or an aromatic group, optionally substituted With at least one group selected from a radical of sulfonic acid, phosphonic acid, phosphonic acid, carboxylic acid, their esters, amides and thiol esters, cyano, trimethylsilyl, hydroxy, alkoxy, halo, nitro, amino, thiol, alkylthio, phenyl;

or an agronomically acceptable salt thereof.

This invention also includes methods to prepare 3,4,4-trifluoro-3-butenoic acid (IV), a key intermediate for the preparation of the compounds of the present invention. These methods are cost effective and/or use intermediates which are not known in the general literature. These methods include:

Refer to Scheme 1

(1a) Hydrolysis of 4-bromo-1,1,2-trifluoro-1-butene (II) with water in N-methylpyrrolidinone to give 3,4,4-trifluoro-3-buten-1-ol (III);

(1b) Jones oxidation of III under specific conditions to give 3,4,4-trifluoro-3-butenoic acid (IV) in 52% overall yield; or Refer to Scheme 2

(2a) A one pot reaction of 1-chloro-1,2-dibromotrifluoroethane (VI) with ethyl vinyl ether in the presence of sodium hydrosulfite/sodium bicarbonate followed by oxidation of the intermediate, 4-bromo-3-chloro-3,4,4-trifluorobutanal (VII), without isolation, with sodium chlorite/hydrogen peroxide to give 4-bromo-3-chloro-3,4,4-trifluorobutanoic acid (VIII) in overall unexpected yields;

(2b) Alternatively, the intermediate VII can be reduced with sodium borohydride without isolation to give 4-bromo-3-chloro-3,4,4-trifluorobutanol ((IX) in high yield; or by hydrolysis of 1,4-dibromo-2-chloro-1,1,2-trifluorobutane (XVI) to give IX. Oxidation of IX with Jones reagent to give VIII in 85% yield.

(2c) Dehalogenation of 4-bromo-3-chloro-3,4,4-trifluorobutanoic acid (VIII) with zinc using conditions analogous to those disclosed in the literature to obtain the desired 3,4,4-trifluoro-3-butenoic add (IV); or Refer to Scheme 3

(3a) A one pot reaction of 1-chloro-1,2-dibromotrifluoroethane (VI) or 1,1,2-trichlorotrifluoroethane (X) with vinylidene chloride in the presence of ammonium persulfate/sodium formate/air in DMF to give 4-bromo-3-chloro-3,4,4-trifluorobutanoic acid (VIII) or 3,4-dichloro-3,4,4-trifluorobutanoic add (XI).

(3b) Dehalogenation of VIII or XI with zinc to give 3,4,4-trifluoro-3-butenoic add (IV).

This invention also includes methods to prepare a compound of the formula I where Q=—(C=O)$R_2$, which comprises:

Refer to Scheme 1

(4a) Reaction of 3,4,4-trifluoro-3-butenoic acid (IV) with oxalyl chloride in the presence of DMF as a catalyst without any solvent to give 3,4,4-trifluoro-3-butenoyl chloride (V).

(4b) Reaction of V with an appropriate reagent in aqueous or aqueous/organic solvent medium in the presence of an acid scavanger such as sodium bicarbonate to give a compound of the formula XVII.

Refer to Scheme 4

(5a) Conversion of VIII to 4-bromo-3-chloro-3,4,4-trifluorobutanoyl chloride (XII) by reacting with appropriate reagents known in the literature, for example, oxalyl chloride.

(5b) Reaction of XII with appropriate reagents in aqueous or aqueous/organic solvent medium in the presence of an acid scavanger such as sodium bicarbonate to give novel compounds XIII, for example, XIV.

(5c) Dehalogenation of XIII with zinc to give compounds of the formula XVII.

(6) The above steps 5a, 5b, or 5c can also be carried out with XI in place of VIII to prepare the compounds of the formula I where Q=—(C=O)$R_2$.

The Steps 4b, 5a, 5b, 5c, and 6 (above) are also useful to prepare compounds of the formula $F_2C=CF—CH_2—(C=O)—R_2$ as disclosed in WO 92/15555 which is incorporated herein by reference.

The compounds IX, XI, XII, and XIV are novel intermediates.

Compounds of the present invention also include, Where possible, hydrated species. Those skilled in the art will recognize that alternate substituents may be identified that will provide substantially equivalent results.

Preferred compounds of this invention are of the formula (I):

$$\begin{array}{c} F \\ \diagdown \\ \diagup \\ F \end{array} C=C-CH_2-Q \quad \quad I$$
$$\phantom{xxxxxxx} | \\ \phantom{xxxxxxxx} F$$

wherein Q is (C=S)-$R_1$ or (C=W)-$R_2$; wherein W is O or S; and $R_1$ and $R_2$ are as described above. Most preferred compounds are where (C=O)$R_2$ and $R_2$ is $NR_7R_8$ where $R_7$ is H and $R_8$ is -$S(O)_2R_{11}$, where $R_{11}$ is alkyl or haloalkyl and their agronomically acceptable salts.

The present invention includes compositions for controlling nematode infestation of a plant comprising an effective amount of a compound of formula I, or an agronomically acceptable salt thereof, in an agronomically acceptable carrier.

The present invention includes a method of systemically controlling nematode, insect or acrid infestation of a plant, comprising applying to a plant locus an effective amount of a formula I or an agronomically acceptable salt thereof.

DETAILED DESCRIPTION OF THE INVENTION

The novel compounds of the present invention are useful for controlling nematode, insect, and acrid infestation of a plant. Many of these compounds, being polar, are highly effective for systemic control, that is, when applied to the foliage or stems of a plant they are able to move through the phloem and xylem of the plant and provide control of nematodes, insects, or acarids at other locations on the plant. It is believed that this control mechanism is a repelling or antifeedant action, rather than a harming action. Others, particularly the nonpolar compounds, are effective only when applied directly to the soil. Some compounds can provide both types of control.

The present methods for systemic control of nematodes, insects, and acarids use the phloem mobile compounds of the present invention or those compounds having sufficient polarity to allow for phloem-mobility without eliminating the nematode-controlling activity of the fluoroalkene moiety. There are several different theories concerning phloem mobility, such as what polarity characteristics compounds must have to be sufficiently phloem mobile in order to be relocated downward in a plant. It has been proposed that the polarity of the molecule as a whole must be sufficient for the molecule to be retained in the phloem, but not be so polar as to not enter at all.

To effectively control nematodes or other pests systemically by application to the above-ground surfaces of a plant, compounds must be capable of passing through the cuticle of the foliage or stem of a plant, passing into the phloem, and remaining there long enough to be transported throughout the plant so as to move to untreated areas including the roots. There they may leak out or in some way contact the posts to such an extent that they are killed or repelled and the damage they would do to the plant is reduced or eliminated. During these stops of transport from the treated areas of leaves or stems throughout the plant, a compound may undergo chemical reactions, such as hydrolysis, or biological reactions, such as enzymatic reactions. In addition, compounds may be devised which, when placed on the plant, prior to absorption into the plant, may undergo reactions that result in a compound that is readily absorbable, translocatable, and effective in preventing pest damage. An example of such compounds are those having UV-labile protecting groups which when exposed to natural light undergo reaction and result in active and mobile compounds. Another example is silylated amine derivatives.

Therefore, what is placed on the foliage or stem of the plant may not be the compound that is actually transported or the compound that actually controls the posts. Thus, the methods of the present invention provide for compounds that may be transformed through chemical or biological reactions to have proper polarity for systemic activity.

The methods of the present invention include applying compounds of the present invention to the plant locus, preferably to the foliage. The compounds can also be applied to the soil or as seed treatments. Also included are compositions comprising an aqueous solution of the active ingredient in an agronomically acceptable carrier.

In addition to the compounds specifically described above, all agronomically acceptable salts of the compounds are within the scope of the present invention. A compound of the present invention having a carboxylic acid or hydroxyl group may exist as the salt having various cations associated therewith, for example, but not limited to, alkali earth metals, such as sodium, calcium, and potassium; magnesium; or quaternary ammonium ions, such as ammonium, mono-, di-, or trialkylammonium, for example, isopropylammonium, or pyridinium.

As used herein, the term "halo", "halide", or "halogen" means fluorine, chlorine, iodine, or bromine or cognates thereof.

The term "alkyl" means straight-chain or branched groups of from one to about seven carbon atoms.

The term "lower alkyl" means a group containing from one to about four carbon atoms.

The term "aliphatic" means saturated or unsaturated, branched or straight-chain, alkyl groups having from one to about ten carbon atoms.

The term "alkoxy" means a lower alkyl group bonded via an oxygen atom.

The term "alkylthio" means a lower alkyl group bonded via a sulfur atom. The term "alkoxycarbonyl" means the lower alkyl ester of a carboxyl group.

The term "aliphatic amine" means an aliphatic group wherein at least one hydrogen is replaced with $-NH_2$.

The term "aliphatic carboxylic acid, amides, esters, and thio esters" means an aliphatic group wherein at least one carbon is a carboxylic group, $-COOH$, or is the lower alkyl ester, amide, or lower alkyl thio ester, thereof.

As used herein, the phrase "amino acid amide of Q" means that $R_6$ is an amino add coupled via a peptide (amide) bond to the $C=O$ of Q. This amino acid may be a natural, i.e., protein, amino add or a nonnaturally occurring amino acid. The amino group of the amino acid may be a substituent of any carbon in the group, for example, alpha, beta, or gamma to the carbonyl.

The term "alkyl or aryl sulfonamide" means a sulfonamide group substituted with a lower alkyl or phenyl group, which in turn may be optionally substituted.

The term "aromatic group" or "aryl" means phenyl, optionally substituted with at least one group selected from hydroxy, alkyl, alkoxy, halo, nitro, amino, thiol, alkylthio, carboxyl, alkoxycarbonyl, and phenyl.

The term "heterocyclic" means any cyclic compound which contains at least one other element other than carbon as a member of the ring. The ring may be saturated or unsaturated. The hetero atom may be oxygen, nitrogen, sulfur, or some other element. Heterocydes include, for example, thiadiazole, pyridine, thiazole, isothiazole, oxazole, imidazole, pyrazole, triazole, benzothiazole, thiophene, furan, and the like, all of which may also be optionally substituted. The carbon atoms of the heterocyclic rings optionally may be substituted with any group or groups which are non-destructive of the nematocidal activity of the compounds. Typical substituents include aliphatic, aromatic and heterocyclic groups, halo, nitro, cyano, alkoxy, alkylthio, haloalkyl, haloalkoxy, halo-, nitro-, cyano- or alkoxy-substituted phenyl, polyhaloalkenylthio, phenylalkylthio, phenylthioalkylthio, propargylthio, cycloalkylmethylthio and the like, further including straight and branched chain structures, and the various isomers of such substituents.

COMPOUND SYNTHESIS

Most of the compounds of the present invention are prepared by reacting 3,4,4-trifluoro-3-butenoyl chloride (V) with appropriate reagent in aqueous or aqueous/organic solvent medium in the presence of an acid scavanger such as sodium bicarbonate.

Synthesis of 3,4,4-trifluoro-3-butenoic acid
Method 1, Scheme 1, Compound IV

The first method involves hydrolysis of 4-bromo-1,1,2-trifluoro-1-butene (II) with water in the presence of N-methyl pyrrolidinone to give 3,4,4-trifluoro-3-buten-1-ol (III), followed by Jones oxidation under conditions not previously known. These conditions are at a temperature of about 51°–54° C. In addition, the 3,4,4-trifluoro-3-buten-1-ol in acetone solvent and the Jones reagent are added to the reaction vessel simultaneously to afford 3,4,4-trifluoro-3-butenoic (IV) add in 52% overall yield.

gave the desired 3,4,4-trifluoro-3-butenoic acid (IV) in 85% yield.

Scheme 1

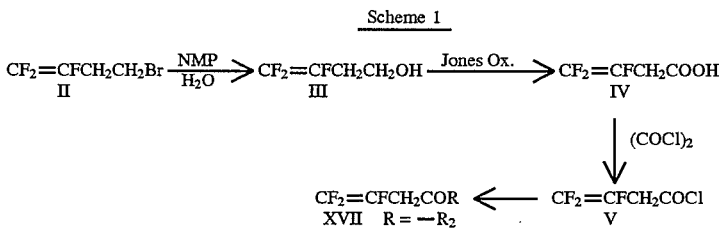

Method 2, Scheme 1, Compound IV

In the second method the synthesis of 4-bromo-3-chloro-3,4,4-trifluoro-butanoic acid (VIII) is followed by zinc dehalogenation to produce 3,4,4-trifluoro-3-butenoic acid (IV).

Scheme 2

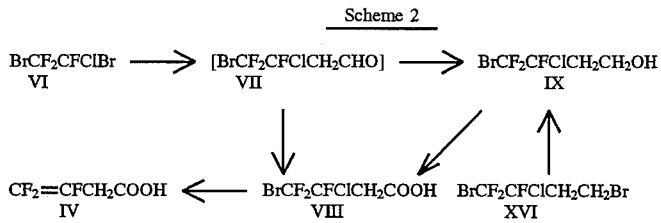

This compound is prepared by reacting 1-chloro-1,2-dibromotrifluoroethane (VI) with ethyl vinyl ether in the presence of sodium dithionite and sodium bicarbonate in a manner analogous to that described in the literature [Huang, Weiyuan; Lu, Long;, Zhang, Yuanfa; *Chin. J. Chem.* 1990, (3), 281]. However, it is now found that the 4-bromo-3-chloro-3,4,4-trifluorobutanal intermediate (VII) is oxidized without isolation with sodium chlorite/hydrogen peroxide. In other words, instead of oxidation with Jones reagent, this method advantageously provides a process which can be carried out in one reaction vessel using preferred reagents and gives an unexpectedly high yield.

Oxidation of VII is also carried out by following reaction conditions similar to those described in Dalconale, D. and Montanari, F; *J. Org. Chem.*, 1986, (51) 567. Alternative oxidation conditions are analogous to those described in the literature [Huang, Weiyuan; Lu, Long;, Zhang, Yuanfa; *Chin. J. Chem.*, 1990, (3), 281; Nwauka, et al., *Tetrahedron Letters*, 1982, 3131; and Yamada, T., et al., *Chemistry Letters*, 1991, 5]. In other words, 4-bromo-3-chloro-3,4,4-trifluorobutanal intermediate can be oxidized to 4-bromo-3-chlore-3,4,4-trifluorobutanoic acid by using various other oxidizing conditions known in the general literature.

Alternatively, the sadehyde intermediate VII can be reduced with sodium berohydride to give the novel compound which is a corresponding alcohol IX in excellent yield. In addition, the alcohol intermediate (IX) can be prepared by hydrolysis of XVI. Jones oxidation of IX gave VIII in 85% yield. Dehalogenation of VIII with zinc in water Method 3, Scheme 3, Compound IV A new method to prepare the desired 3,4,4-trifluoro-3-butenoic acid (IV) involves a one pot reaction of 1-chlore-1,2-dibromotrifluorethane (VI) or 1,1,2-trichlorotrifluoroethane (X) with vinylidene chloride in the presence of ammonium persulfate/sodium formate/air in DMF to give directly 4-bromo-3-chloro-3,4,4-trifluorobutanoic acid (VIII) or novel compound 3,4-dichloro-3,4,4-trifluoro-butanoic acid (XI). The reaction conditions to prepare XI from X are similiar to those described in Hu, Chang-Ming; Qing, Feng-Ling; Zhang, Hong-Gen; *J. Fluorine Chem.*, 1990, (49) 275–280. The formation of XI in the above reaction was confirmed by GC/MS (EI): m/z 212 (M++2), 210 (M+), 195, 193, 157, 155, 127,125, 107,105, 89, 69, 45. Dehalogenation of VIII or XI with zinc gives IV.

Scheme 3

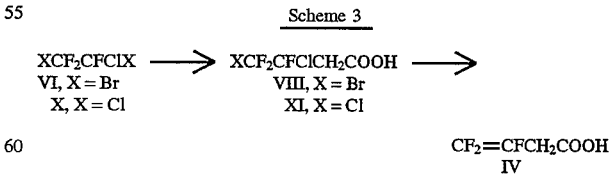

The compounds of formula XVII can also be prepared by an alternate method to prepare selected compounds of formula I as exemplified with XV shown in Scheme 4. The reaction sequence shown in Scheme 4 using novel intermediates XII and XIII exemplified by XIV can also be carried out by substituting XI in place of VIII to prepare compounds of formula XVII.

Scheme 4

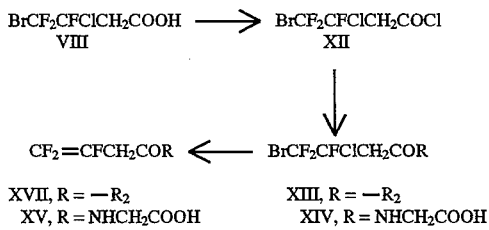

XVII, R = —R$_2$
XV, R = NHCH$_2$COOH

XIII, R = —R$_2$
XIV, R = NHCH$_2$COOH

Synthesis of 3,4,4-trifluoro-3-butenoic acid
Method 1,Scheme 1, Compound IV

A mixture of 4-bromo-1,1,2-trifluoro-1-butene (II) (3.0 kg, 16.67 mol) water (1.51 L, 83.9 mol) and N-methylpyrrolidinone (9.06 L) in a 22 L 4-necked round-bottom flask was heated at reflux under nitrogen for 20 h. Water (4.53 L) was added and the solution was distilled through a 50 cm Vigreux column in tandem with a Dean-Stark trap to maintain a constant water volume in the pot. The lower layer in the trap (azeotrope bp 96°–100.6° C.) was drawn off periodically as the distillation progressed to give 3,4,4-trifluoro-3-buten-1-ol (III) (1706 g, 81.2%) as a clear liquid, which is used directly in the next step.

A mechanically stirred 12 L glass reactor dad with a jacket cooled with tap water was charged with 100 mL of acetone and 100 mL of Jones reagent. A solution of 3,4,4-trifluoro-3-buten-1-ol (850 g, 6.75 mol) diluted to a total volume of 5.0 L in acetone was added simultaneously with 5.0 L of Jones reagent via a twin head peristaltic pump capable of a pump rate ca. 120 mL/min. A reaction temperature of 51°–54° C. was maintained by adjusting the pump rate and the tap water cooling flow. Following the addition (45 min), the mixture was allowed to cool to 35°–40° C. over 30–60 min. The reaction mixture was transferred to a separatory funnel and layers separated. The upper layer was washed once with brine and concentrated. The lower layer was diluted with water (500 mL) and extracted with dichloromethane (3 L). The dichloromethane extract was combined with the above residue, washed with brine and dried over magnesium sulfate. Evaporation of the solvent gave 613 g (65%) of the desired product as a green oil.

Method 2, Scheme 2, Compound IV

A one L. 3-necked flask equipped with a mechanical stirrer was charged with sodium bicarbonate (15.2 g, 181 mmole), potassium dihydrogen phosphate (8.2 g, 60.3 mmol), sodium hydrosulfite (3.15 g, 18.1 mmol) and water (100 mL). After the solids were dissolved, acetonitrile (200 mL) was added and the mixture was cooled to 5°–10° C. A mixture of 1,2-dibromo-1-chlorotrifluoroethane (VI) (50 g, 181 mmol) and ethyl vinyl ether (18.1 g, 250 mmol, 24 mL) was taken in a dropping funnel, and approx. 20% was added rapidly with stirring. After one or two minutes, a slight exotherm (2 or 3 degrees raise in temperature) occurred. Following that, addition was continued while keeping the internal temperature at 10°–15° C. After the addition was complete (10 min), the mixture was stirred for another 15 min at 10°–15° C. GC analysis of an aliquot in ether indicated completion of the reaction.

The above mixture was cooled to 5° C. and 30% hydrogen peroxide (23.59 g, 208 mmol) was added first two or three mL dropwise (exotherm) and the remaining in one portion. A solution of sodium chlorite (80% assay, 23.1 g, 204 mmol) in 75 mL, of water was added dropwise with stirring while keeping the internal temperature 10°–15° C. (exothermic reaction). The addition took approx. 30 min. After the addition was complete, the mixture was stirred at 15° C. for 30 min and at room temperature for another 60 min. GC analysis of an aliquot indicated the reaction was essentially complete. The mixture was cooled to ca. 10° C. and sodium sulfite (7.5 g) was added in portions with stirring. After 10 min of stirring, peroxide test (starch iodide paper) indicated negative. The mixture was treated with 20 mL of 6N HCl and transferred to a separatory funnel. The top organic layer was separated and concentrated on a rotary evaporator to a weight of 58.7 g.

The above crude bromochlorotrifluorobutanoic acid (58.7 g) was treated with 50 mL of water and cooled in ice-water bath. Zinc dust (15.0 g, 0.230 gatom) was added in portions with stirring. The reaction is very exothermic but does not hurt the formation of the desired product; in fact it accelerates the reaction. After the addition was complete (20 min), the mixture was stirred at room temperature until exotherm subsided (another 20 min). The mixture was transferred to a separatory funnel by pouring through a plug of glass wool (to remove chunks of zinc salts), diluted with 6N HCl (ca. 25 mL) and extracted with dichloromethane (2×100 mL). The dichloromethane extract (top layer) was washed with 6N HCl (30 mL) and brine (100 mL) and dried over anhyd. MgSO$_4$. Evaporation of the solvent gave 19.28 g (76% for the two steps) of the crude 3,4,4-trifluoro-3-butenoic acid (IV) as a pale yellow liquid Synthesis of 3,4-dichlore-3,4,4-trifluorobutanoic acid
Scheme 3, Compound XI A mixture of 1,1,2-trichlorotrifluorethane (X) (9.37 g, 50 mmol), vinylidene chloride (4.85 g, 50 mmol), ammonium persulfate (11.41 g, 50 mmol), sodium formate (3.4 g, 50 mmol) and water (1.8 g, 0.1 mol) in DMF (80 mL,) was stirred (dry-ice/acetone condensor) at room temperature with air bubbling. After 30 min, an aliquot of the reaction mixture was acidified with dilute HCl, extracted with ether and analyzed by GC, which indicated the formation of two products. These products were identified by GC/MS (EI) as 4-chloro-3,4,4-trifluoro-2-butenoic acid and novel compound 3,4-dichloro-3,4,4-trifluorobutanoic acid (XI). The compound XI gives 3,4,4-trifluoro-3-butenoic acid (IV) upon reaction with zinc. Under the above reaction conditions, 1-chloro-1,2-dibromotrifluoroethane (VI) gave 3-chloro-4-bromo-3,4,4-trifluorobutanoic acid (VIII) as one of the products.

Synthesis of 4-bromo-3-chloro-3,4,4-trifluorobutanol
Method 1, Scheme 2, Compound IX A mixture of 1,4-dibromo-2-chloro-1,1,2-trifluorobutane (XVI) (7.5 g, 24.6 mmol), 1-methyl-2-pyrrolidinone (14 mL) and water (2.5 mL) was heated at 130° C. for 16 hours. The mixture was cooled to room temperature, diluted with water (80 mL) and extracted with ether (2×75 mL). The ether extract was washed with water (3×40 mL,), brine, and dried over anhydrous magnesium sulfate. The residue obtained after evaporation of the solvent was chromatographed over silica gel to give 2.9 g (49%) of the desired alcohol as a clear off.

Method 2, Scheme 2, Compound IX

A solution of sodium hydrosulfite (34.8 g, 0.2 mol) and sodium bicarbonate (22.0 g, 0.262 mol) in water (400 mL) was treated with 400 mL of THF and the mixture was cooled to 5° C. A mixture of 1,2-dibromo-1-chlorotrifluoroethane (VI) (55.26 g, 0.2 mol) and ethyl vinyl ether (21.6 g, 0.3 mol) was added in one portion to the above mixture with stirring and cooling. The mixture was then stirred at 10°–15° C. for 30 min and then solid sodium chloride was added to saturate the aqueous layer. The aqueous layer was separated and extracted with THF (100 mL). The combined THF extract was diluted with water (100 mL) and treated with sodium borohydride (7.57 g, 0.2 mol) in portions with stirring and cooling (ice-water bath). The mixture was stiffed for 30 min and then acidified 3N HCl by dropwise addition.

The aqueous layer was saturated with sodium chloride and the organic layer was separated, washed with brine and dried over anhydrous magnesium sulfate. The residue obtained after evaporation of the solvent was distilled under vacuum to give 37.7 g (78%) of the desired alcohol as a clear oil, bp 98°–100° C./40 mmHg.

Jones oxidation of 4-bromo-3-chloro-3,4,4-trifluorobutanol Scheme 2, Compound IX A solution of 4-bromo-3-chloro-3,4,4-trifluorobutanol (IX) (2.41 g, 10 mmol) in acetone (35 mL) was treated with Jones reagent (7.5 mL) in 10 min with stirring and cooling (ice-water bath). The mixture was then stirred at room temperature for 30 min and 0.5 mL of i-propanol was then added. The precipitated salts were removed by filtration, washed with acetone. The residue obtained after concentration of the flitrate was dissolved in methylene chloride (100 mL), washed with 1N HCl (50 mL), brine, and dried over anhydrous magnesium sulfate. Evaporation of the solvent gave 2.17 g (85%) of 4-bromo-3-chloro-3,4,4-trifluorobutanoic acid (VIII) as a dear oil.

Synthesis of N-(3,4,4-trifluoro-1-oxo-3-butenyl)glycine Scheme 4, Compound XV

A mixture of 4-bromo-3-chloro-3,4,4-trifluorobutanoic acid (8.0 g, 31 mmol), oxalyl chloride (5.8 g, 45 mmol) and two drops of DMF in methylene chloride (40 mL) was stirred at room temperature for 16 hours. The solvent and excess oxalyl chloride were removed by rotary evaporation to give 8.1 g (95%) of the crude product (XII) as an yellow liquid.

The above acid chloride (5.7 g, 20.8 mmol) with out any further purification was added to an ice-cold solution of sodium hydroxide (1.6 g, 40 mmol), glycine (3.06 g, 40 mmol) in water (15 mL) with stirring. The mixture was stirred in cold for 2.5 hours, acidified with conc. HCl, and extracted with ethyl acetate (2×75 mL). The ethyl acetate extract was washed with brine and dried over anhydrous magnesium sulfate. Evaporation of the solvent gave 6.33 g (97%) of the crude product (XIV) as a yellow gum. Proten NMR spectral analysis of the above crude product indicated the formation of the desired product.

The above crude product (5.77 g, 18.5 mmol) was dissolved in ethanol (15 mL), water (10 mL) and treated with zinc dust (1.2 g) in portions with stirring and cooling (tap water). The mixture was then stirred at room temperature for 10 min filtered and extracted with ethyl acetate (2×100 mL). The ethyl acetate extract was washed with brine and dried over anhydrous magnesium sulfate. Evaporation of the solvent gave a white solid, which was triturated with anhydrous ether, filtered and air dried to give 1.65 g (45%) of the desired product (XV).

Synthesis of 3,4,4-Trifluoro-3-butenyl chloride and Derivatives
Scheme 1, Compound V A mixture of 3,4,4-trifluoro-3-butenoic acid (IV) (19.28 g, 138 mmol), oxalyl chloride (21.8 g, 172 mmol; 15 mL) and two drops of DMF was stirred for 6 hours and distilled at atmospheric pressure under nitrogen. The fraction boiling at 90°–98° C. was collected to give 16.1 g (74%) of the desired product as a clear liquid.

The compounds of the present invention are merely illustrated by the following working examples, but are not limited thereto. The example numbers which follow correspond to the same example numbers of the structures and biological data presented below.

EXAMPLE 1

Phosphonic acid, [[(3,4,4-trifluoro-1-oxo-3 butenyl) amino] methyl]-, disodium salt:

A stirred ice-cold mixture of sodium bicarbonate (1.26 g, 15 mmol) and di-t-butyl aminomethanephosphonate (2.23 g, 10 mmol) in water (20 mL,) and dichloromethane (40 mL) was treated dropwise with 3,4,4-trifluoro-3-butenoyl chloride (1.58 g, 10 mmol). After the addition was complete, the mixture was stirred at room temperature for 30 min and the organic layer was washed with brine and dried over anhydrous magnesium sulfate.

Evaporation of the solvent gave 2.98 g (86%) of the desired di-t-butyl ester, which was dissolved in 15 mL, of trifluoroacetic acid and allowed to stand at room temperature for 30 min. The residue obtained after evaporation of the trifluoroacetic acid was partitioned between ethyl acetate (50 mL) and water (25 mL). Concentration of the aqueous layer gave 1.5 g of the free acid which was redissolved in water (20 mL) with 1.08 g (12.87 mmol). The solution was concentrated to dryness to give 1.98 g of the title compound as a pale yellow solid. mp 190°–200° C.

EXAMPLE 5

2-(3,4,4-trifluoro-1-oxo-3-butenyl)amino-4,6-dimethoxy-pyrimidine

To an ice-cooled stirred suspension of 2-amino-4,6-dimethoxypyrimidine (1.55 g, 10 mmol) in dichloromethane (50 mL) and potassium carbonate (2.76 g, 20 mmol) in water (20 mL) was added 3,4,4-trifluoro-3-butenoyl chloride (3.17 g, 20 mmol). The reaction mixture was stirred in cold for 10 min and at r.t. for 15 min. The organic layer was washed with 3 N HCl (2×25 mL,), saturated sodium bicarbonate (25 mL) and brine, and dried. Evaporation of the solvent gave 0.296 g (10%) of the title compound as a white solid. m.p. 127°–130° C.

EXAMPLE 7

4-[(3,4,4-trifluoro-1-oxo-3-butenyl)amino]-benzenesulfonic acid

To an ice-cooled solution of sulfanilic acid (3.90 g, 20 mmol) and sodium bicarbonate (1.68 g, 20 mol) in water (30 mL,) was added 3,4,4-trifluoro-3-butenoyl chloride (3.17 g, 20 mol) in 5 min with stirring. The mixture was stirred in cold for 15 min and at r.t. for one hour. The solution was acidified with 8.0 mL, of 25% sulfuric acid with cooling and then extracted with n-butanol (2×60 mL). The organic layer was washed with brine and concentrated and the residue was triturated with ether, filtered and dried to give 4.2 g of a white solid. The proton NMR spectum of this material indicated the presence of approx. 90% of the desired product and 10% of unreacted sulfanilic acid. This material was redissolved in 75 mL of n-butanol and washed twice with 6N HCl (30 and 15 mL) and brine. The residue obtained after evaporation of the solvent was treated with methanol/ether and filtered. Evaporation of the filtrate gave 0.61 g (10%) of the desired product as a white solid. m.p.>300° C.

EXAMPLE 9

3,4,4-trifluoro-N-[(trifluoromethyl)sulfonyl]-3-butenanmide

To an ice-cooled solution of trifluoromethanesulfonnmide (2.75 g, 18.4 mmol) in 7.4 mL of 2.5 N sodium hydroxide was added 3,4,4-trifluoro-3-butenoyl chloride (2.93 g, 18.5 mmol) with stirring in 2 min. The mixture was stirred in cold for 30 min and the white precipitate formed was filtered, washed with cold water (10 mL,) and dried to give 0.82 g (16%) of the desired product as a white solid. m.p. 115°–120° C.

EXAMPLE 11

1-(3,4,4-trifluoro-1-oxo-3-butenyl)-1H-1,2,4-triazole

To a solution of 1,2,4-triazole (1.38 g, 20 mmol) in ethyl acetate (100 mL) was added 3,4,4-trifluoro-3-butenoyl chloride (1.59 g, 10 mmol) at r.t. with stirring. The mixture was stirred for 30 min end filtered. The residue obtained after evaporation of the solvent was redissolved in dichloromethane (25 mL) end filtered. Evaporation of the solvent gave 1.8 g (94%) of the desired product as a clear oil.

EXAMPLE 13

3,4,4-trifluoro-N-phenyl-3-butenethioamide

A mixture of 3,4,4-trifluoro-N-phenyl-3-butenamide (1.0 g, 4.65 mmol) end phosphorus pentasulfide (2.07 g, 4.65 mmol) in anhyd. THF (100 mL) was heated at reflux under nitrogen for 1 hour. The reaction mixture was cooled to r.t. and filtered. The filtrate was concentrated and the residue was chromatographed over silica gel (dichloromethane/hexanes, 80/20) to give 0.65 g (60%) of the desired compound as a pale yellow solid. m.p. 65°–67° C.

EXAMPLE 15

3-Butenethioic acid, 3,4,4-trifluoro-, s-[2-(trimethylsilyl)ethyl] ester

To an ice-cooled suspension of 2-(trimethylsilyl) ethanethiol (1.0 g, 7.5 mmol) in dichloremethane (35 mL) and 10% aqueous sodium hydroxide (6.0 mL) was added 3,4,4-trifluoro-3-butenoyl chloride (2.38 g, 15 mmol) with stirring. The mixture was stirred in cold for 30 min end the organic layer was washed with saturated sodium bicarbonate and brine, and dried. The residue obtained after evaporation of the solvent was kugelrohr distilled at 0.5 mmHg (pot temperature 50°–60° C.) to give 1.1 g (56%) of the title compound as a clear oil.

EXAMPLE 17

Diethyl (2,3,3-trifluoro-2-propenyl)phosphonate

An ice-cooled solution of 2,3,3-trifluoro-2-propen-1-ol (11.2 g, 0.1 mole) and two drops of pyridine in dry ether (100 mL) was treated with phosphorus tribromide (9.47 g, 0.035 mole), and the mixture was stirred in cold for one hour and at r.t. for overnight. The solution was washed with 5% sodium bicarbonate and brine, and dried. The solvent was distilled off using a 15 cm vigreaux column to give 14.0 g (80%) of 2,3,3-trifluoro-2-prepenyl bromide.

A solution of 2,3,3-trifluoro-2-propenyl bromide (5.25 g, 30 mmol) and triethyl phosphite (4.15 g, 25 mmol) in acetonitrile (15 mL) was heated at reflux for overnight. The residue obtained after evaporation of the solvent was chromatographed over silica gel (hexanes/ethyl acetate/ethanol, 80/20/1) to give diethyl (1,1,2-trifluoro-2-propenyl) phosphonate (0.8 g, 11%) and diethyl (2,3,3-trifluoro-2-propenyl)phosphonate (1.0 g, 14%).

EXAMPLE 18

2,3,3-trifluoro-2-propenylphosphonic acid

A solution of di-t-butyl hydroxymethylphosphonate (2.0 g, 8.9 mmol) and triethylamine (1.27 g, 12.6 mmol) in dichloromethane (15 mL) was treated dropwise with a solution of triflic anhydride (1.8 mL, 10.72 mmol) in dichloremethane (5 mL) at −78° C. maintaining the internal temperature <−50° C. The solution was warmed to −30° C. and then recooled to −78° C. and poured onto 100 mL of hexanes and 30 mL of saturated sodium bicarbonate solution. The organic phase was washed with water and brine, and dried. Evaporation of the solvent gave 3.18 g (100%) of (di-t-butylphosphinyl)-methyl trifluoromethylsulfonate as a light brown oil.

An ice-cooled solution of trifluoroethylenylzinc bromide (11.2 mmol) in anhyd. DMF (13 mL) was first stirred with copper(I)bromide (0.8 g, 5.57 mmol) for 30 min and allowed to reach r.t. To this solution was added (di-t-butylphosphinyl)methyl trifluoromethylsulfonate (2.5 g, 7.0 mmol) and stirred at r.t. for 4 hours and at 40°–45° C. for 30 min. The reaction mixture was then poured onto 30 mL. of saturated ammonium chloride and 100 mL of ether. The aqueous layer was extracted once again with 50 mL of ether and the combined ether extracts were washed with saturated sodium bicabonate, water and brine, and dried. The residue (0.9 g) obtained after evaporation of the solvent was chromatographed over silica gel (25/75, ethyl acetate/hexanes) to give 0.5 g of di-t-butyl 2,3,3-trifluoro-2-propenylphosphonate as a yellow oil.

The above di-t-butylphosphonate (0.5 g) was dissolved in 3 mL of methanol and treated with 0.5 mL of 3 N HCl and allowed to stand at r.t. for 30 min. The solution was concentrated and the residue was redissolved in 10 mL of water and washed with 10 mL of ether. Evaporation of the aqueous layer gave 0.14 g of 2,3,3-trifluoro-2-propenylphosphonic acid as a yellow oil.

EXAMPLE 19

Sodium 2,3,3-trifluoro-2-propenylphenylphosphinate

An ice-cooled solution of trifluoroethylene zinc bromide (11.2 mmol) in anhyd. DMF (13 mL) was first stirred with copper(I)bromide (0.8 g, 5.57 mmol) for 30 min and allowed to reach r.t. To this solution was added (t-butoxyphenylphosphinyl)methyl trifluoromethane sulfonate (2.0 g, 5.55 mmol) and stirred at r.t. for 4 hours and at 40°–45° C. for 30 min. The reaction mixture was then poured onto 40 mL of saturated ammonium chloride and 5 mL of 3 N HCl and extracted with ethyl acetate twice (75 and 50 mL). The combined ethyl acetate extract was washed with water (2×50 mL), and extracted with 5% sodium bicarbonate (2×15 mL). The sodium bicarbonate extract was acidified with conc. HCl with cooling and extracted with ethyl acetate (3×40 mL). The combined ethyl acetate extracts were washed with brine and dried. Evaporation of the solvent gave 0.62 g of a brown viscous material which was dissolved in 2.5 mL of water containing 0.22 g of sodium bicarbonate and purified by HPLC (C-18 reverse phase, water/acetonitrile) to give 0.254 g of the title compound as a white solid. m.p. 278°–279° C.

EXAMPLE 20

3,4,4-trifluoro-1-(2-methylphenyl)-3-buten-1-one

To a solution of 3,4,4-trifluoro-3-butenoyl chloride (3.75 g, 23.65 mmol) in anhyd. ether (100 mL) was treated with copper(I)iodide (2.28 g, 12 mmol) followed by 24 mL of 1.0M solution of benzylmagnesium chloride in ether dropwise at −78° C. with stirring under nitrogen The reaction mixture was stirred at -78° C. for 10 min and allowed to reach to r.t. and filtered. The filtrate was successively washed with 2N HCl 5% sodium bicarbonate and brine, and dried. The residue, a mixture of several products, obtained after evaporation of the solvent was chromatographed over silica gel (20% hexanes in dichloromethane) and the major product (least polar) was isolated and further purified by kugelrohr distillation, b.p. 130°–140° C. (pot temperature)

12 mmHg. Proton and fluorine NMR spectra of this material was found to correspond to the title compound.

Examples 2 and 6 are likewise prepared in a manner analogous to Example 5 using the appropriate starting materials.

Example 12 is prepared in a manner analogous to Example 11 using the appropriate starting material.

Examples 3, 4, 8, 10, 14, and 16 are prepared in a manner analogous to Example 15 using the appropriate starting materials.

The following table describes the chemical structures of the examples.

| Example Number | Name | Structure |
|---|---|---|
| 1 | PHOSPHONIC ACID, [[3,4,4-TRIFLUORO-1-OXO-3-BUTENYL)AMINO]METHYL]-, DISODIUM SALT, DIHYDRATE MP: 190.0–200.0 | 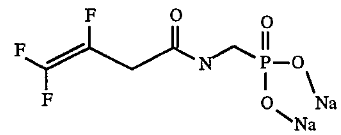 |
| 2 | 3-BUTENAMIDE, N-(CYANOMETHYL)-3,4,4-TRIFLUORO- MP: 56.0–60.0 | 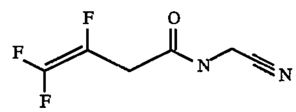 |
| 3 | 3-BUTENAMIDE, 3,4,4-TRIFLUORO-N-METHOXY- MP: 46.0–49.0 | 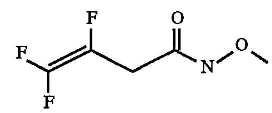 |
| 4 | 3-BUTENOIC ACID, 3,4,4-TRIFLUORO-, 2-(AMINOCARBONYL)HYDRAZIDE MP: 132.0–138.0 | 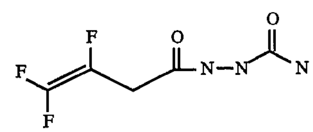 |
| 5 | 3-BUTENAMIDE, N-(4,6-DIMETHOXY-2-PYRIMIDINYL)-3,4-4-TRIFLUORO- MP: 127.0–130.0 | 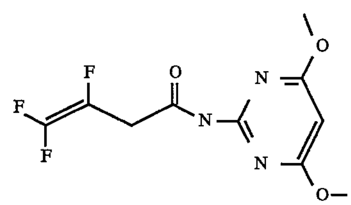 |
| 6 | 3-BUTENAMIDE, 3,4,4-TRIFLUORO-N-(PHENYLMETHYL)-N-[(TRIMETHYLSILYL)METHYL]- Oil | 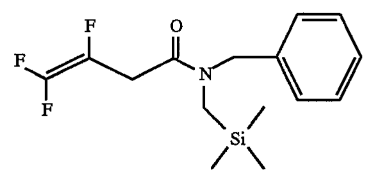 |
| 7 | BENZENESULFONIC ACID, 4-[(3,4,4-TRIFLUORO-1-OXO-3-BUTENYL)AMINO]- MP: 300.0 | 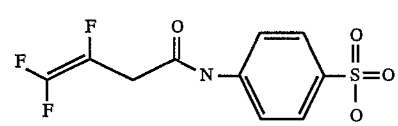 |
| 8 | 3-BUTENAMIDE, 3,4,4-TRIFLUORO-N-(METHYLSULFONYL)- MP: 114.0–120.0 | 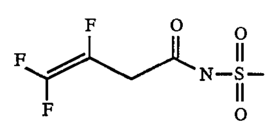 |
| 9 | 3-BUTENAMIDE, 3,4,4-TRIFLUORO-, N-[(TRIFLUOROMETHYL)-SULFONYL]- MP: 115.0–120.0 | 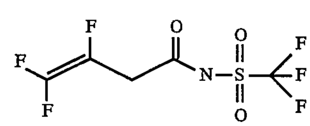 |
| 10 | METHANESULFONIC ACID, [(3,4,4-TRIFLUORO-1-OXO-3-BUTENYL)AMINO]- MP: 264.0–267.0 | 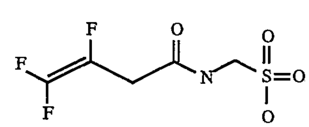 |

-continued

| Example Number | Name | Structure |
|---|---|---|
| 11 | 1H-1,2,4-TRIAZOLE, 1-(3,4,4-TRIFLUORO-1-OXO-3-BUTENYL)- Oil | 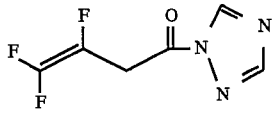 |
| 12 | 1H-PYRAZOLE, 1-(3,4,4-TRIFLUORO-1-OXO-3-BUTENYL)- Oil | 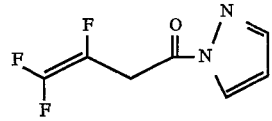 |
| 13 | 3-BUTENETHIOAMIDE, 3,4,4-TRIFLUORO-N-PHENYL- MP: 65.0–67.0 | 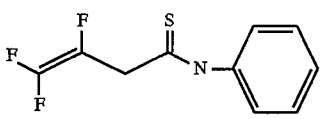 |
| 14 | 3-BUTENOIC ACID, 3,4,4-TRIFLUORO-, 3-(TRIMETHYLSILYL)PROPYL ESTER Oil | 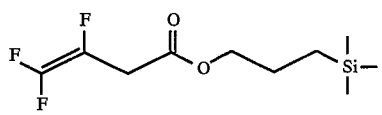 |
| 15 | 3-BUTENETHIOIC ACID, 3,4,4-TRIFLUORO-, S-[2-(TRIMETHYLSILYL)ETHYL] ESTER Oil | 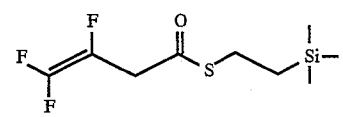 |
| 16 | 3-BUTENETHIOIC ACID, 3,4,4-TRIFLUORO-, S-2-PYRIMIDINYL ESTER Oil | 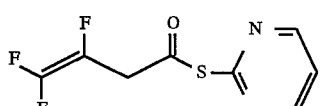 |
| 17 | PHOSPHONIC ACID, (2,3,3-TRIFLUORO-2-PROPENYL)-, DIETHYL ESTER Oil | 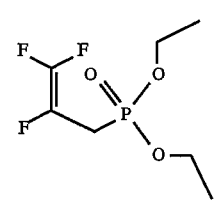 |
| 18 | PHOSPHONIC ACID, (2,3,3-TRIFLUORO-2-PROPENYL)- Oil | 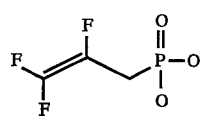 |
| 19 | PHOSPHINIC ACID, PHENYL(2,3,3-TRIFLUORO-2-PROPENYL)-, SODIUM SALT MP: 278.0–279.0 | 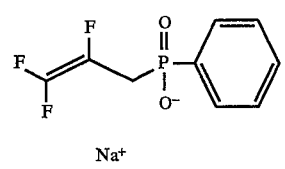 |
| 20 | 3-BUTEN-1-ONE, 3,4,4-TRIFLUORO-1-(2-METHYL PHENYL)- Oil | 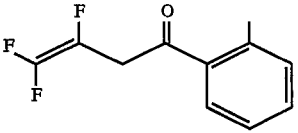 |

Compounds of formula I are prepared by methods analogous to those described herein or known in the literature using starting materials described herein or known in literature or which can be prepared by methods analogous to those in the literature.

COMPOSITIONS

In normal use, the compounds usually will not be employed free from admixture or dilution, but ordinarily will be used in a suitable formulated composition compatible with the method of application and comprising an effective amount of the compound. The compounds of this invention, like most agricultural agents, may be blended with agriculturally acceptable surface-active agents and carriers normally employed for facilitating the dispersion of active ingredients, recognizing the accepted fact that the formulation and mode of application may affect the activity of the material.

The present compounds may be applied to the above ground portion of plants or they may applied to the soil. The present compounds may be applied, for example, as sprays, dusts, seed treatments or granules, to the area where post control is desired, the type of application varying with the post and the environment. Thus, the compounds of this invention may be formulated as granules of large particle size, as powdery dusts, as wettable powders, as emulsifiable concentrates, as solution, and the like.

Granules may comprise porous or nonporous particles, such as attapulgite day or sand, for example, which serve as carriers for the present compounds. The granule particles are relatively large, a diameter of about 400–2500 microns typically. The particles are either impregnated with the compound of the invention from solution or coated with the compound, adhesive sometimes being employed. Granules generally contain 0.05–10%, preferably 0.5–5%, active ingredient.

Dusts are admixtures of the compounds, with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the compound. These finely divided solids have an average particle size of less than about 50 microns. A typical dust formulation contains 1 part of compound and 99 parts of talc.

The compounds of the present invention may be made into liquid concentrates by dissolution or emulsification in suitable liquids and into solid concentrates by admixture with talc, days, and other known solid carriers used in the agricultural chemical art. The concentrates are compositions containing about 5–50% active compound and 95-50% inert material, which includes surface-active dispersing, emulsifying, and wetting agents, but even higher concentrations of active ingredient may be employed experientally. The concentrates are diluted with water or other liquids for practical application as sprays, or with additional solid carrier for use as dusts.

A typical 50% wettable powder formulation would consist of 50.0% (wt/wt) of active ingredient, 22.0% attapulgite diluent, 22.0% of kaolin diluent, and 6.0% sodium salts of sulfonated Kraft lignin emulsifier.

Typical carriers for solid concentrates (also called wettable powders) include fuller's earth, clays, silicas, and other highly absorbent, readily wetted inorganic diluents. A suitable solid concentrate formulation may contain 1.5 parts each of sodium lignosulfonate and sodium lauryl sulfate as wetting agents, 25 parts of active compound and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the active compound with a liquid or solid emulsifying agent, or they may also contain a liquid carrier such as xylene, heavy aromatic naphthas, isophorone and other relatively non-volatile organic solvents. For application, these concentrates are dispersed in water or other liquid carders and normally applied as sprays to areas to be treated.

A typical 50 gram per liter emulsifiable concentrate formulation would consist of 5.9% (wt/wt) of a compound of the invention; as emulsifiers; 1.80% of a blend of the calcium salt of dodecylbenzene sulfonate and nonionic 6-molar ethylene oxide condensation product of nonylphenol, 2.70% of a blend of the calcium salt of dodecylbenzene sulfonate and a nonionic 30-molar ethylene oxide condensation product of nonylphenol, 1.50% of a nonionic paste of polyalkylene glycol ether, and 88.10% refined xylene solvent.

Typical surface-active wetting, dispersing, and emulsifying agents used in agricultural formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oil; sulfonated petroleum oils; fatty acid esters of polyhydric alcohols and the ethylene oxide addition products of such esters; and the addition products of long-chain mercaptans and ethylene oxide. The surface active agent normally comprises about 1–15% by weight of the active ingredient.

Other useful formulations include simple solutions of the active ingredient in a solvent in which it is completely soluble at the desired concentration, such as water, acetone, or other organic solvents. The preferred formulation for foliar application is an aqueous solution, more preferably containing glycerin and a surfactant, such as Tween®20, and most preferably 1% glycerin and 0.1% Tween®20.

The compositions may be formulated and applied with suitable pesticidal active ingredients, including insecticides, acaricides, fungicides, plant regulators, herbicides, fertilizers, etc.

METHODS OF USE BIOLOGICAL EVALUATION METHOD

Compounds of the present invention, prepared as described above, were tested for effectiveness in controlling root knot nematodes (*Meloidogyne incognita*) on tomato roots when applied to foliage of young plants.

Tomato plants, cv 'Rutgers', were grown one per pot in six cm square plastic pots containing a mixture of equal parts fine sand, coarse sand, silt loam soil, and commercial potting medium. A 10,000 ppm stock solution of each test compound was prepared in either water or acetone. Samples were then diluted with additional water to give final test concentrations of 500 and 100 ppm. Tween®20 was added for a final concentration of 0.5% v/v in all test samples.

When the tomato plants were 18–21 days old the test solutions were sprayed onto the leaves and stems. Each rate of each test compound was applied to three tomato plants using four ml of spray solution per plant. One day after spraying the plants were inoculated with mature root knot nematode eggs containing J1 larvae, with 8,000 eggs per plant applied in 5 ml of water on soil at the stem base. Plants then were incubated in a growth chamber at 27° C. with all replicate pots randomized throughout the chamber. During the two weeks immediately following application of the test compounds all plants received sub-irrigation and the foliage was kept dry.

After three weeks incubation the plant roots were washed and nematode disease severity was assessed. Each root system was rated individually and a visual estimate of the percent of the root system afflicted with nematode galling was determined. Values of 0, 1, 5, 10, 20, 30, 40, 50, 60, 70, 80, or 100 percent galled roots were assigned to each plant. Non-treated plants generally received root ratings of 60% disease or greater. For each treatment (compound & rate) a standard deviation was calculated for the mean of the three replicate plants. Percent disease control relative to non-treated plants also was calculated.

TABLE 1

Mean percent root disease (galled), the standard deviation of that mean (std dev), and percent control of root disease relative to non-treated plants.

| Example | ppm | % disease | std dev | % control |
|---------|-----|-----------|---------|-----------|
| 1 | 500 | 80 | 0.00 | 0* |
| 1 | 100 | 87 | 4.71 | −8 |
| 2 | 500 | 67 | 11.55 | 17 |
| 2 | 100 | 73 | 11.55 | 8 |
| 3 | 500 | 70 | 20.00 | 20 |
| 3 | 100 | 77 | 11.55 | 12 |
| 4 | 500 | 73 | 5.77 | 8 |
| 4 | 100 | 80 | 0.00 | 0* |
| 5 | 500 | 30 | 20.00 | 66 |
| 5 | 100 | 90 | 0.00 | −3 |
| 6 | 500 | 87 | 5.77 | 0* |
| 6 | 100 | 85 | 7.07 | 2 |
| 7 | 500 | 17 | 5.77 | 69 |
| 7 | 100 | 23 | 5.77 | 56 |
| 8 | 500 | 5 | 0.00 | 94 |
| 8 | 100 | 80 | 0.00 | 0* |
| 9 | 500 | 5 | 0.00 | 94 |
| 9 | 100 | 80 | 0.00 | 0* |
| 10 | 500 | 27 | 11.55 | 50 |
| 10 | 100 | 20 | 10.00 | 62 |
| 11 | 500 | 7 | 2.89 | 92 |
| 11 | 100 | 80 | 0.00 | 0* |
| 12 | 500 | 43 | 15.28 | 46 |
| 12 | 100 | 80 | 0.00 | 0* |
| 13 | 500 | 27 | 15.28 | 50 |
| 13 | 100 | 40 | 10.00 | 25 |
| 14 | 500 | 80 | 0.00 | 8 |
| 14 | 100 | 83 | 5.77 | 4 |
| 15 | 500 | 90 | 0.00 | −3 |
| 15 | 100 | 85 | 7.07 | 2 |
| 16 | 500 | 50 | 10.00 | 38 |
| 16 | 100 | 80 | 0.00 | 0* |
| 17 | 500 | 27 | 15.28 | 50 |
| 17 | 100 | 30 | 10.00 | 44 |
| 18 | 500 | 73 | 5.77 | 0* |
| 18 | 100 | 77 | 5.77 | −5 |
| 19 | 500 | 73 | 5.77 | 0* |
| 19 | 100 | 73 | 5.77 | 0* |
| 20 | 500 | 47 | 11.55 | 12 |
| 20 | 100 | 53 | 5.77 | 0* |

*= no biological activity at the rate tested

What is claimed is:

1. A compound having the structure:

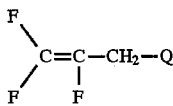

wherein q is -(P=W)$R_3R_4$; wherein W is O or S;

$R_3$ and $R_4$ are independently $R_{15}$, —$OR_{15}$, -$SR_{15}$, -$NR_{15}R_{16}$ where $R_{15}$ and $R_{16}$ are independently selected from the group consisting of an aromatic group, optionally substituted with at least one group selected from a radical of sulfonic acid, phosphonic acid, phosphonic acid, carboxylic acid, their esters, amides and thiol esters, cyano, trimethylsilyl, hydroxy, alkoxy, halo, nitro, amino, thiol, alkylthio, phenyl, or any agronomically acceptable salt thereof.

2. A compound of claim 1 wherein $R_3$ and $R_4$ are independently $R_{15}$, —$OR_{15}$ or -$SR_{15}$.

3. A compound of claim 1 wherein $R_3$ and $R_4$ are independently -$NR_{15}R_{16}$.

4. A compound having the structure:

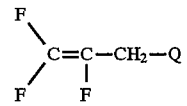

wherein Q is -(P=W)$R_3R_4$; wherein W is O;

$R_3$ and $R_4$ are independently —$OR_{15}$, where $R_{15}$ is independently selected from the group consisting of an aromatic group, optionally substituted with at least one group selected from a radical of sulfonic acid, phosphonic acid, phosphonic acid, carboxylic acid, their esters, amides and thiol esters, cyano, trimethylsilyl, hydroxy, alkoxy, halo, nitro, amino, thiol, alkylthio, phenyl, or any agronomically acceptable salt thereof.

5. A compound having the structure:

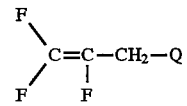

wherein Q is -(P=W)$R_3R_4$; wherein W is O;

$R_3$ and $R_4$ are independently $R_{16}$, where $R_{16}$ is independently selected from the group consisting of an aliphatic or an aromatic group, optionally substituted with at least one group selected from a radical of sulfonic acid, phosphonic acid, phosphonic acid, carboxylic acid, their esters, amides and thiol esters, cyano, trimethylsilyl, hydroxy, alkoxy, halo, nitro, amino, thiol, alkylthio, phenyl, or any agronomically acceptable salt thereof.

6. A composition for controlling nematode infestation of a plant comprising an effective amount of a compound of claim 5 in an agronomically acceptable carrier.

7. A composition for controlling nematode infestation of a plant comprising an effective amount of a compound of claim 1 in an agronomically acceptable carrier.

8. A method of systemically controlling nematode, insect or acrid infestation of a plant, comprising applying to a plant locus an effective amount of a compound having the structure:

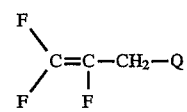

wherein Q is -(P=W)$R_3R_4$; wherein W is O;

$R_3$ and $R_4$ are independently —$OR_{15}$, where $R_{15}$ is independently selected from the group consisting of an aromatic group, optionally substituted with at least one group selected from a radical of sulfonic acid, phosphonic acid, phosphonic acid, carboxylic acid, their esters, amides and thiol esters, cyano, trimethylsilyl, hydroxy, alkoxy, halo, nitro, amino, thiol, alkylthio, phenyl, or any agronomically acceptable salt thereof.

9. A method of systemically controlling nematode, insect or acrid infestation of a plant, comprising applying to a plant locus an effective amount of a compound having the structure:

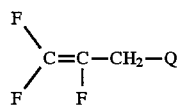

wherein Q is -(P=W)$R_3R_4$; wherein W is O;

$R_3$ and $R_4$ are independently $R_{16}$, where $R_{16}$ is independently selected from the group consisting of an aliphatic or an aromatic group, optionally substituted with at least one group selected from a radical of sulfonic acid, phosphonic acid, phosphonic acid, carboxylic acid, their esters, amides and thiol esters, cyano, trimethylsilyl, hydroxy, alkoxy, halo, nitro, amino, thiol, alkylthio, phenyl, or any agronomically acceptable salt thereof.

* * * * *

UNITED STATES PATENT AND TRADEMARK OFFICE
CERTIFICATE OF CORRECTION

PATENT NO.    :  5,627,174

DATED         :  May 6, 1997

INVENTOR(S)   :  Phillion et al.

It is certified that error appears in the above-identified patent and that said Letters Patent is hereby corrected as shown below:

Column 21, Claim 1, line 61, delete "q" and insert --Q--.

Column 21, Claim 1, line 67, delete "phosphonic" and insert --phosphinic--.

Column 22, Claim 4, line 20, delete "phosphonic" and insert --phosphinic--.

Column 22, Claim 4, line 36, delete second occurrence of "phosphonic" and insert --phosphinic--.

Column 22, Claim 8, line 62, delete "phosphonic" and insert --phosphinic--.

Column 24, Claim 9, line 5, delete second occurrence of "phosphonic" and insert --phosphinic--.

Signed and Sealed this

Twenty-fifth Day of August, 1998

Attest:

BRUCE LEHMAN

*Attesting Officer*   *Commissioner of Patents and Trademarks*